United States Patent [19]

Werblin

[11] Patent Number: 5,222,981

[45] Date of Patent: Jun. 29, 1993

[54] MULTI-COMPONENT INTRAOCULAR LENS

[75] Inventor: Theodore P. Werblin, Bluefield, W. Va.

[73] Assignee: Werblin Research & Development Corp., Princeton, W. Va.

[21] Appl. No.: 745,354

[22] Filed: Aug. 15, 1991

[51] Int. Cl.$^5$ .............................. A61F 2/16
[52] U.S. Cl. .......................................... 623/6
[58] Field of Search ............................. 623/6

[56] References Cited

U.S. PATENT DOCUMENTS

| | | | |
|---|---|---|---|
| 3,458,870 | 8/1969 | Stone, Jr. | 623/5 |
| 3,945,054 | 3/1976 | Fedorov et al. | 623/5 |
| 4,373,218 | 2/1983 | Schacher | 623/6 |
| 4,402,579 | 9/1983 | Poler | 623/6 |
| 4,575,373 | 3/1986 | Johnson | 623/6 |
| 4,585,456 | 4/1986 | Blackmore | 623/6 |
| 4,585,457 | 4/1986 | Kalb | 623/6 |
| 4,685,921 | 8/1987 | Peyman | 623/6 |
| 4,685,922 | 8/1987 | Peyman | 623/6 |
| 4,731,078 | 3/1988 | Stoy et al. | 623/6 |
| 4,778,463 | 10/1988 | Hetland | 623/6 |
| 4,932,971 | 6/1990 | Kelman | 623/6 |
| 4,950,289 | 8/1990 | Krasner | 623/6 |

OTHER PUBLICATIONS

Werblin et al. "Epikeratophakia: The surgical correction of aphakia. III. Preliminary results of a prospective clinical trial," 93 Arch. Opth., pp. 342–347 (1982).

Werblin et al. "Hydrogel Keratophakia: Measurement of Intraocular Pressure," vol. 11, No. 4 CLAO Journal, pp. 354–357 (Oct. 1985).

Werblin et al. "Refractive Corneal Surgery: The Use of Implantable Alloplastic Lens Material," 11 Austrial Journal of Opthalmology, pp. 325–331 (1983).

Werblin "Lamellar Refractive Surgery: Where Have We Been And Where Are We Going?" vol. 5, No. 3, Refractive and Corneal Surgery, pp. 167–176 (Jan. 1989).

Binder et al. "Hydrogel Refractive Keratoplasty. Lens Removal and Exchanges" vol. 2, Cornea at pp. 119–125.

*Primary Examiner*—Randy C. Shay
*Attorney, Agent, or Firm*—Arent, Fox, Kintner, Plotkin & Kahn

[57] ABSTRACT

The multi-component intraocular lens for an eye includes a base intraocular lens, a cap situated on the base lens, a plurality of flanges for attaching the cap on the base lens, at least one sandwiched lens which is sandwiched between the base intraocular lens and the cap, and a plurality of projections holding the multi-component intraocular lens in place in the eye, wherein the base intraocular lens forms a platform on which to place the other components and the cap forms an enclosure holding the sandwiched lens in a desired position.

26 Claims, 6 Drawing Sheets

FIG. 6B(1)
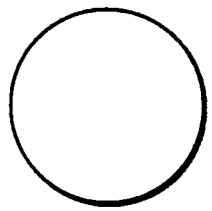
FIG. 6B(2)
FIG. 6B(3)
FIG. 6B(4)
FIG. 6B(5)
FIG. 6D
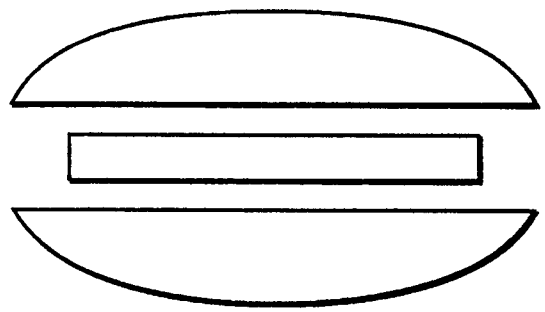

FIG. 6C(1)
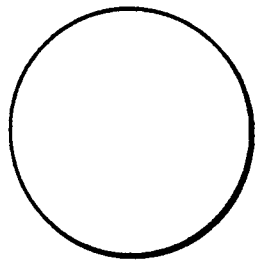
FIG. 6C(2)
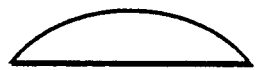
FIG. 6C(3)
FIG. 6C(4)
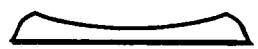
FIG. 6C(5)
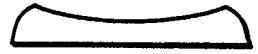
FIG. 6C(6)
FIG. 6C(7)
FIG. 6C(8)
FIG. 6C(9)
FIG. 6C(10)
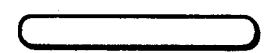
FIG. 6C(11)

MULTI-COMPONENT INTRAOCULAR LENS

BACKGROUND OF THE INVENTION

The present invention relates to a multi-component intraocular lens for an eye.

Traditionally, surgery to remove the crystalline lens of the eye has a refractive accuracy of ±10%. Additionally, traditional intraocular lenses could not be modified once they were in place in the patient's eye. The only way the vision characteristics of an intraocular lens could be modified was to use spectacles or contact lenses after surgery or to remove the existing implanted lens and to replace it with one having the desired vision characteristics. Due to tissue growth around the haptics or other position fixation means used to maintain the already implanted lens in the eye, as well as adhesion of eye tissue to other portions of the implant, especially where that lens has been implanted for an extended period of time, removal of the intraocular lens involved relatively major and complex surgery and the risk of loss of vision.

Accordingly, there is a need for an intraocular lens which can be modified once it is in place within the eye. Moreover, there is a need for an intraocular lens which can, in addition to correcting cataracts, be used to correct any refractive (i.e., vision) problem.

Additionally, there is a need for an easily manufacturable intraocular lens which can be designed so that there is no need to custom manufacture a unique intraocular lens for every possible type of vision correction.

SUMMARY OF THE INVENTION

It is therefore an object of the present invention to provide a multi-component intraocular lens which can be modified once it is in place within an eye.

It is a further object of the present invention to provide a multi-component intraocular lens which is designed so that it can correct any refractive problem.

It is also an object of the present invention to provide a multi-component intraocular lens which is designed so that the manufacturer does not need to custom manufacture every possible type of lens for any possible refractive problem.

Additional objects and advantages of the invention will be set forth in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, a multi-component intraocular lens for an eye comprises a base intraocular lens; a cap situated on the base intraocular lens; a plurality of flanges for attaching the cap on the base intraocular lens; at least one sandwiched lens sandwiched between the base intraocular lens and the cap; and a plurality of projections holding the multi-component intraocular lens in place in the eye, wherein the base intraocular lens forms a platform on which to place the other components and the cap forms an enclosure holding the at least one sandwiched lens in a desired position.

The accompanying drawings, which are incorporated in and constitute a part of this specification, illustrate one embodiment of the invention and, together with this description, serve to explain the principles of the invention.

BRIEF DESCRIPTION OF THE DRAWINGS

FIG. 2B is a top view of the securing screws;

FIGS. 6A-6D are views of the various components. FIG. 6A(1) is a top view of the base intraocular lens; FIG. 6A(2) is a 90° cross-sectional view of a plus power base intraocular lens; and FIG. 6A(3) is a 180° cross-sectional view of a plus power base intraocular lens. FIG. 6B(1) is a top view of the sandwiched lens; FIG. 6B(2) is a 90° cross-sectional view of a sandwiched lens shaped for the correction of astigmatism; FIG. 6B(3) is a 180° cross-sectional view of a sandwiched lens shaped for the correction of astigmatism; FIG. 6B(4) is a 90° cross-sectional view of a blank sandwiched lens; and FIG. 6B(5) is a 180° cross-sectional view of a blank sandwiched lens. FIG. 6C(1) is a top view of the cap lens; FIG. 6C(2) is a 90° cross-sectional view of a plus power cap lens; FIG. 6C(3) is a 180° cross-sectional view of a plus power cap lens; FIG. 6C(4) is a 90° cross-sectional view of a minus power cap lens; FIG. 6C(5) is a 180° cross-sectional view of a minus power cap lens; FIG. 6C(6) is a 90° cross-sectional view of a plus power cap lens with a multi-focal component; FIG. 6C(7) is a 180° cross-sectional view of a plus power cap lens with a multi-focal component; FIG. 6C(8) is a 90° cross-sectional view of a minus power cap lens with a multi-focal component; FIG. 6C(9) is a 180° cross-sectional view of a minus power cap lens with a multi-focal component; FIG. 6C(10) is a 90° cross-sectional view of a blank cap lens; and FIG. 6C(11) is a 180° cross-sectional view of a blank cap lens. FIG. 6D is a cross-sectional view of the multicomponent intraocular lens of the present invention.

DESCRIPTION OF THE PREFERRED EMBODIMENT

Figure 1A:
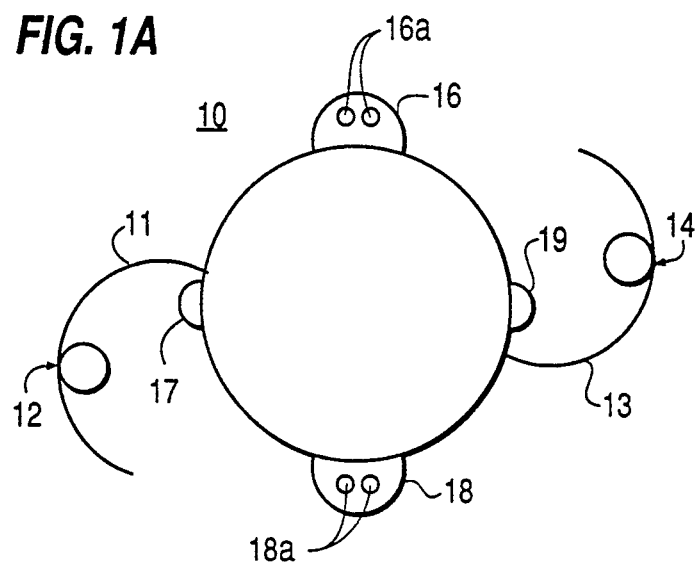
FIGS. 1A-1C are top views of the three components of the multi-component intraocular lens in accordance with a preferred embodiment of the present invention.

Reference will now be made in detail to the present preferred embodiment of the invention, an example of which is illustrated in the accompanying drawings in which like reference characters refer to corresponding elements.

The multi-component intraocular lens of the present invention can be used to correct any refractive (i.e., vision) problem, not only for the correction of cataracts. It is also designed in such a way that the manufacturer does not need to custom manufacture a single lens for every possible type of vision problem, but only needs to manufacture a limited number of designs. Additionally, the multi-component intraocular lens of the present invention provides an improvement over prior intraocular lens constructions in that modifications to vision characteristics of the lens may be made once the lens system is in place. It is not necessary to remove the entire underlying lens in a complex surgical procedure.

Figure 1B:
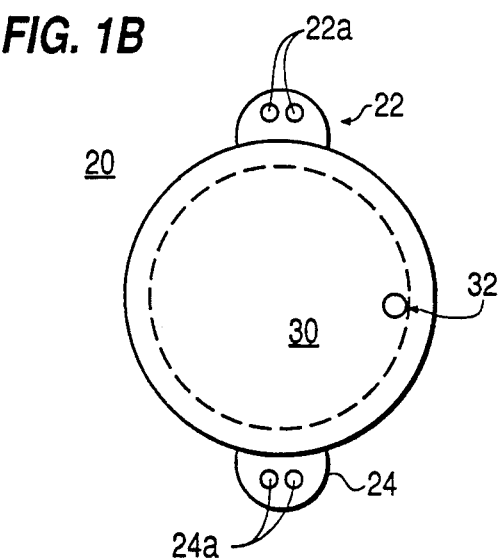
Figure 1C:
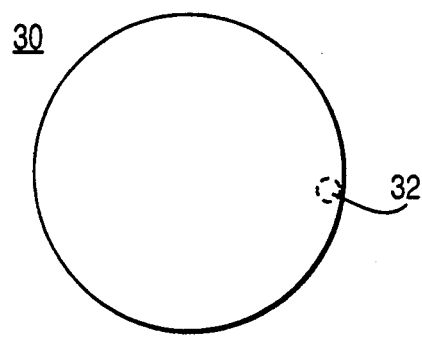

FIGS. 1A–1C are top views illustrating the three separate components of the multi-component intraocular lens in accordance with the present preferred embodiment of the invention. In accordance with the present invention, the multi-component intraocular lens for an eye comprises a base intraocular lens. The base intraocular lens 10 is illustrated in FIG. 1A. The multi-component intraocular lens also includes a cap 20 as shown in FIG. 1B which is situated on the base lens 10. The base intraocular lens 10 includes a plurality of securing flanges 16 and 18. The cap 20 also includes a plurality of securing flanges 22 and 24. Flanges 22 and 24 each include a plurality of unthreaded screw holes 22a and 24a, respectively. Flanges 16 and 18 each include a plurality of threaded screw holes 16a, and 18a, respectively.

Figure 2A:
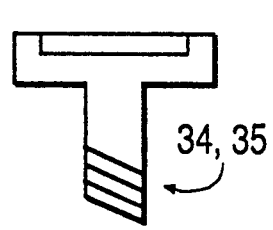
FIG. 2A is a side view of the securing screws for uniting the base intraocular lens to the cap in accordance with a preferred embodiment of the present invention.
Figure 2A:
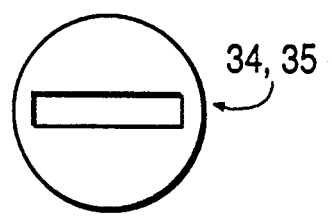
Figure 2C:
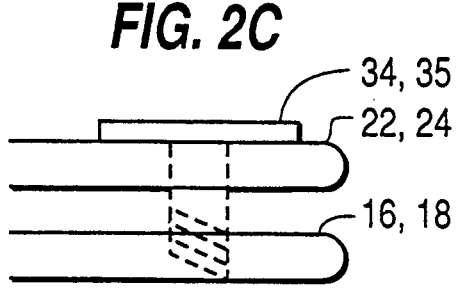
FIG. 2C is a side view illustrating the use of the securing screws in accordance with a preferred embodiment of the present invention.

FIGS. 2A–2C illustrate securing screws 34 and 35 which are threaded into one of each of screw holes 16a and 18a and through the corresponding one of each of screw holes 22a and 24a for attaching the cap 20 on the base lens 10. The extra ones of screw holes 16a, 18a, 22a and 24a are used for back-up purposes. Flanges 16 and 18 are used to attach the base lens 10 to the cap 20.

The multi-component intraocular lens further includes at least one sandwiched lens 30, as illustrated in FIG. 1C, which is sandwiched between the base lens 10 and the cap 20. The multi-component intraocular lens also includes a plurality of projections 11 and 13 which hold the multi-component intraocular lens in place in the eye, wherein the base intraocular lens 10 forms a platform on which to place the other components and the cap 20 forms an enclosure holding the sandwiched lens 30 in the desired position. The sandwiched lens 30 is held in place in cap 20 in the enclosure formed by cap 20. The plurality of projections 11 and 13 are disposed at concordantly selected respective distances on the base intraocular lens 10. The plurality of projections 11 and 13 each include a capsular fixation hole, such as 12 and 14 around which the eye tissue may form to hold the lens system in place.

In the preferred embodiment, in accordance with routine cataract surgery, the base lens 10 replaces the crystalline lens of the eye. Additionally, the base lens 10 modifies the overall focusing capacity of the eye. The base lens 10 has a diameter of between 5 millimeters to 10 millimeters. The cap 20 has a diameter of between 5 millimeters to 10 millimeters. The sandwiched lens has a diameter of between 3 millimeters to 9 millimeters. Preferably, the base lens 10 is comprised of polymethylmethacrylate ("PMMA"). Flanges 16, 17, 18 and 19 are also comprised of PMMA. The cap 20 is comprised of a silicone or acrylic material. Flanges 22 and 24 are also comprised of a silicone or acrylic material. The sandwiched lens 30 may also be comprised of PMMA. Securing screws 34 and 35 may be comprised of PMMA or prolene. The plurality of projections 11 and 13 are comprised of PMMA or prolene.

As stated above, the multi-component intraocular lens of the present invention may be implanted into an eye of a patient in accordance with existing cataract intraocular lens surgery procedures. Initially, the cap 20 and the sandwiched lens 30 may be blank lenses, as shown in FIGS. 6B and 6C without any corrective factor. Once the patient's eye heals after the cataract surgery has been performed, a second surgical procedure may be utilized to replace the blank lenses with a cap lens 20 with the desired optical characteristics to correct the patient's refractive problem. The blank sandwiched lens 30 may also be replaced with a lens shaped for the correction of astigmatism as shown in FIG. 6B. In accordance with the multi-component intraocular lens of the present invention, the cap 20 and the sandwiched lens 30 are removable without removal of the base intraocular lens 10. Additional surgical procedures of this type may be performed as needed until the desired optical characteristics are achieved.

In accordance with the preferred embodiment of the present invention, and as shown in FIG. 1C, the sandwiched lens 30 includes an optical marker 32 thereon such that rotation of the sandwiched lens 30 enables correct placement of the sandwiched lens 30 for correction of astigmatism. In this manner, multi-component intraocular lenses in accordance with the present invention do not need to be custom manufactured for the wearer, but only a small number of lenses need be designed due to the fact that the sandwiched lens 30 may be rotated for correct placement in the individual wearer's eye.

Figure 4A:
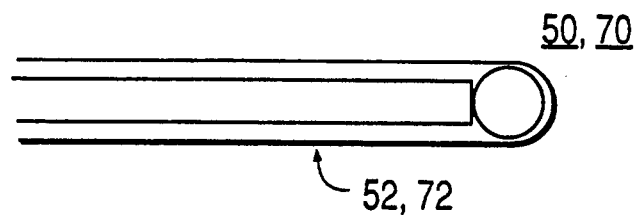
FIG. 4 is a side view of a detachment tool to be used during removal of the initial cap and sandwiched lens components and an attachment tool to be used during implantation of a supplemental cap and sandwiched lens in accordance with a preferred embodiment of the present invention.
Figure 4B:
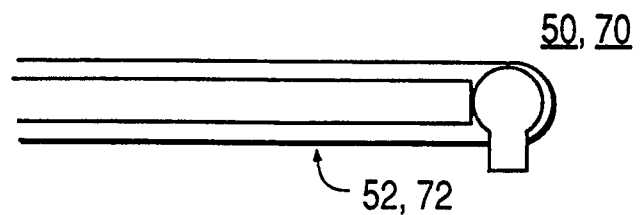
Figure 3A:
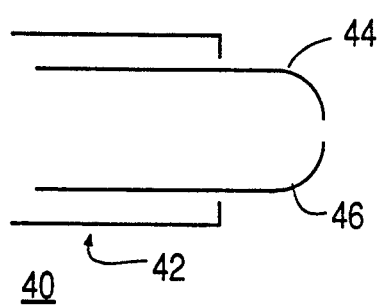
FIGS. 3A-3C are side views of a holding tool to be used during removal or substitution of the cap and sandwiched lens components of the multi-component intraocular lens of the present invention.
Figure 3B:
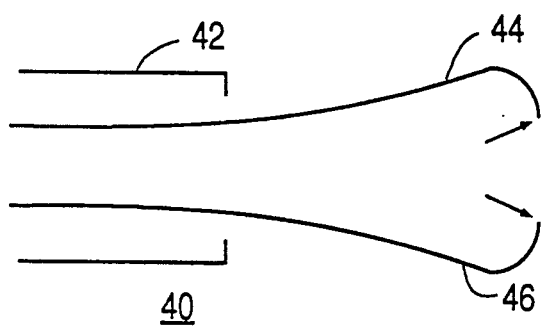
Figure 3C:
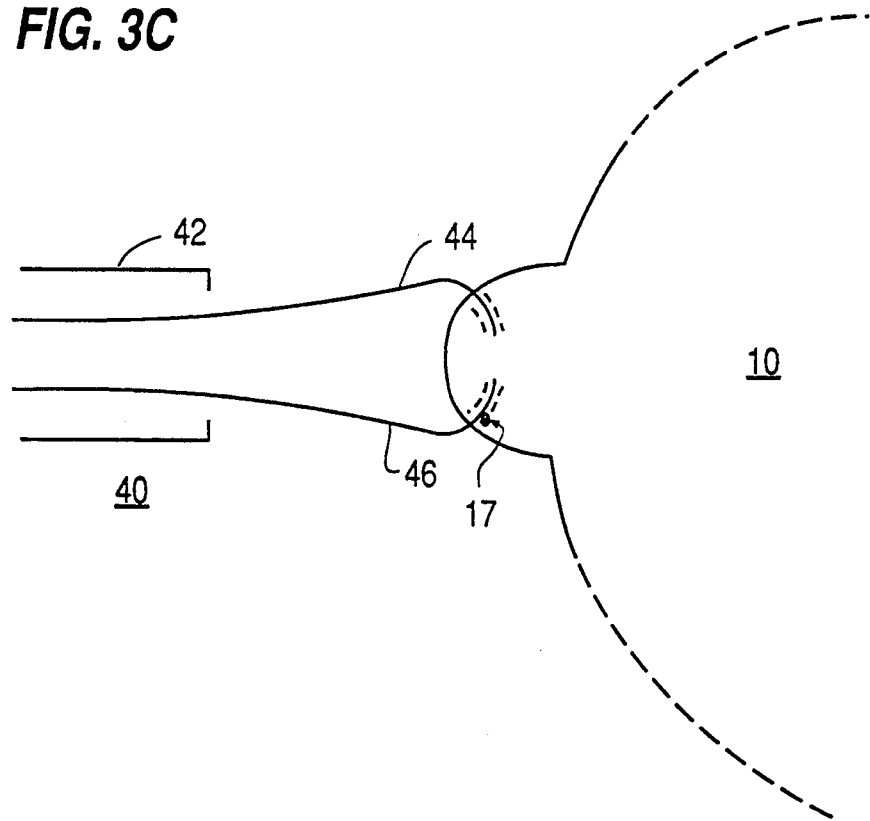

Special tools have been designed for utilization with the multi-component intraocular lens of the present invention. In order to perform the operation involving removal of the cap 20 and the sandwiched lens 30 from the base 10, a first instrument, a holding tool, as shown in FIGS. 3A and 3B, has been designed. This first instrument 40 grabs onto the base lens 10 as shown in FIG. 3C. The first instrument 40 makes use of the flanges 17 or 19 for attachment purposes. The first instrument 40 is held by the fingers utilizing a holding device or fingergrip (not shown) on the sleeves 42 on either side of the first instrument 40. Pressing of the fingers on this fingergrip drives components located in the sleeve which open and close jaws 44 and 46. Preferably, jaws 44 and 46 grab the flanges 17 and 19 of the base lens 10. As shown in FIG. 4, a detachment tool, which is similar to a screwdriver, is then used to detach the initial cap 20 and sandwiched lens 30 from the base lens 10. When tool 50 is used for detachment purposes, it is inserted into screw holes 22a and 24a. A counter-clockwise rotation of tool 50 is used for detachment. The instrument 50 includes sleeves 52 on either side for holding the instrument 50 with the hand.

After removal of the original cap 20 and sandwiched lens 30, a supplemental cap 20 and sandwiched lens 30 may then be attached onto the base lens 10 utilizing the first instrument 40 to grab onto the base lens 10 and hold the base lens 10. While the base lens 10 is held in position by the first instrument 40, the attachment tool 70, shown in FIG. 4, simultaneously screws the securing screws 34 and 35 into threaded screw holes 16a and 18a on the base lens 10 and through the unthreaded screw holes 22a and 24a on supplemental cap 20 by using a clockwise rotation of tool 70 and thereby attaches the cap 20 on the base lens 10 and encloses the sandwiched lens 30 into the enclosure. The instrument 70 includes sleeves 72 on either side for holding the instrument 70 with the hand.

Figure 5A:
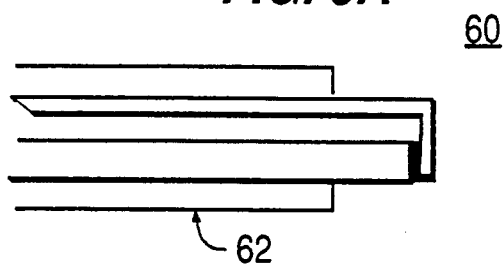
FIGS. 5A-5B are side views of a cutting tool to be used if the detachment tool fails during removal of the cap and sandwiched lens components of the multi-component intraocular lens from the eye i accordance with a preferred embodiment of the present invention.
Figure 5B:
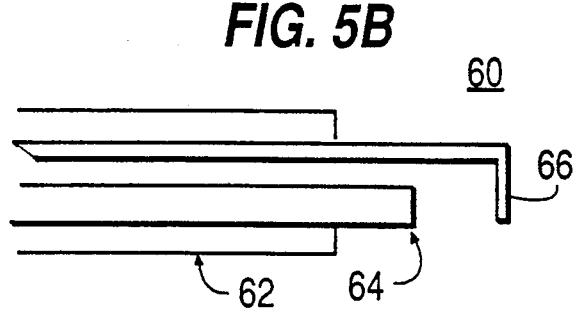
Figure 5B:
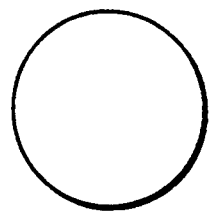
Figure 5B:
Figure 5B:

If the detachment operation described above is unsuccessful, a fourth instrument 60, a cutting tool, as shown in FIGS. 5A and 5B, may be used to detach the flanges 17 and 19 of the base lens 10 for removing the cap 20 and the sandwiched lens 30. Cutting Tool 60 includes sleeves 62, a cutting blade 64 and a clamp 66. The user's fingers may press against sleeves 62 to initiate the clamping action of clamp 66 to stop cutting.

Preferably, the first, second, third and fourth instruments 40, 50, 60 and 70 are comprised of surgical stainless steel.

The supplemental cap 20 may be shaped to provide it with the optical characteristics for producing a resultant bifocal optical system, as shown in FIG. 6C. Alternatively, the cap 20 may be shaped to provide it with the optical characteristics for producing a resultant multi-focal optical system to correct presbyopia, as shown in FIG. 6C. Or, the cap 20 may have a power to correct hyperopia in the eye. Additionally, the cap 20 may have a power to correct myopia in the eye. The shape of the particular cap 20 which is used would depend on the vision needs of the particular patient concerned.

As described above, the supplemental sandwiched lens 30 may be shaped for correction of astigmatism. Thus, the resultant multi-component intraocular lens may be formed so as to correct any refractive vision problem of a patient and is not limited merely to correction of cataracts.

It will be apparent to those skilled in the art that various modifications and variations can be made in the multi-component intraocular lens of the present invention without departing from the scope or spirit of the invention. Thus, it is intended that the present invention cover the modifications and variations of this invention provided they come within the scope of the appended claims and their equivalents.

What is claimed is:

1. A multi-component intraocular lens for an eye comprising:
   a base intraocular lens, said base intraocular lens having a radius and a circumference;
   a cap situated on said base intraocular lens;
   a plurality of flanges, one subset of said plurality of flanges being connected to said base intraocular lens and a second subset of said plurality of flanges being connected to said cap, for attaching the cap on said base intraocular lens;
   at least one sandwiched lens shaped for correction of astigmatism and sandwiched between said base intraocular lens and said cap; and
   a plurality of projections, connected to said base intraocular lens, for holding said multi-component intraocular lens in place in the eye, wherein said base intraocular lens forms a platform on which to place the other components and said cap forms an enclosure holding the at least one sandwiched lens in a desired orientation.

2. The multi-component intraocular lens as claimed in claim 1 wherein said cap and said at least one sandwiched lens are removable from the eye without removal from the eye of said base intraocular lens.

3. The multi-component intraocular lens as claimed in claim 2 wherein said at least one sandwiched lens is a blank lens.

4. The multi-component intraocular lens as claimed in claim 2 wherein said sandwiched lens includes an optical marker thereon such that rotation of said sandwiched lens enables correct placement of said sandwiched lens for correction of astigmatism.

5. The multi-component intraocular lens as claimed in claim 2 wherein said cap and said at least one sandwiched lens are reinsertable onto said base lens.

6. The multi-component intraocular lens as claimed in claim 1 wherein the base lens has a diameter of 5 mm to 10 mm.

7. The multi-component intraocular lens as claimed in claim 1 wherein the cap has a diameter of 5 mm to 10 mm.

8. The multi-component intraocular lens as claimed in claim 1 wherein the sandwiched lens has a diameter of 3 mm to 9 mm.

9. The multi-component intraocular lens as claimed in claim 1 wherein the plurality of projections are disposed at predetermined selected respective sites around the radius of the base intraocular lens.

10. The multi-component intraocular lens as claimed in claim 1 wherein said cap is shaped to provide said multi-component intraocular lens with the optical characteristics for producing a resultant bifocal optical system.

11. The multi-component intraocular lens as claimed in claim 1 wherein said cap is shaped to provide said multi-component intraocular lens with the optical characteristics for producing a resultant multi-focal optical system.

12. The multi-component intraocular lens as claimed in claim 1, wherein said cap is a blank lens.

13. The multi-component intraocular lens as claimed in claim 1 wherein said plurality of flanges are comprised of PMMA.

14. The multi-component intraocular lens as claimed in claim 1 wherein the plurality of projections are comprised of PMMA.

15. The multi-component intraocular lens as claimed in claim 1 wherein the base lens is comprised of PMMA.

16. The multi-component intraocular lens as claimed in claim 1 wherein the cap is comprised of a silicone or acrylic material.

17. The multi-component intraocular lens as claimed in claim 1 wherein the at least one sandwiched lens is comprised of PMMA.

18. The multi-component intraocular lens as claimed in claim 1 wherein the base lens modifies the overall focusing capacity of the eye.

19. The multi-component intraocular lens as claimed in claim 1 wherein the cap has a power to correct hyperopia in the eye.

20. The multi-component intraocular lens as claimed in claim 1 wherein the cap has a power to correct hyperopia in the eye.

21. The multi-component intraocular lens as claimed in claim 1 wherein the cap has a power to correct myopia in the eye.

22. The multi-component intraocular lens as claimed in claim 1 wherein the cap has a power to correct myopia in the eye.

23. The multi-component intraocular lens as claimed in claim 1 wherein the cap has a multi-focal capacity to correct presbyopia in the eye.

24. The multi-component intraocular lens as claimed in claim 1 wherein the cap has a multi-focal capacity to correct presbyopia in the eye.

25. A multi-component intraocular lens for an eye comprising:
- a base intraocular lens;
- a cap situated on said base intraocular lens;
- a plurality of securing screws;
- a plurality of flanges, one subset of said plurality of flanges being connected to said base intraocular lens and including a plurality of threaded screw holes and a second subset of said plurality of flanges being connected to said cap, said second subset including a plurality of unthreaded screw holes, wherein said plurality of securing screws are threaded into said unthreaded screw holes and said threaded screw holes to attach said base intraocular lens to said cap;
- at least one sandwiched lens shaped for correction of astigmatism and sandwiched between said base intraocular lens and said cap, and
- a plurality of projections, connected to said base intraocular lens, for holding said multi-component intraocular lens in place in the eye, wherein said base intraocular lens forms a platform on which to place the other components and said cap forms an enclosure holding the at least one sandwiched lens in a desired orientation.

26. A method of providing a multi-component intraocular lens for an eye, said multi-component intraocular lens having
- a base intraocular lens, said base intraocular lens having a radius and a circumference,
- a cap situated on said base intraocular lens,
- a plurality of flanges, one subset of said plurality of flanges being connected to said base intraocular lens and a second subset of said plurality of flanges being connected to said cap, for attaching the cap on said base intraocular lens,
- at least one sandwiched lens sandwiched between said base intraocular lens and said cap, and
- a plurality of projections, connected to said base intraocular lens, for holding said multi-component intraocular lens in place in the eye, wherein said base intraocular lens forms a platform on which to place the other components and said cap forms an enclosure holding the at least one sandwiched lens in a desired position, said method comprising the steps of: implanting the multi-component intraocular lens into an eye of a patient; and removing the cap and the at least one sandwiched lens as needed.

* * * * *